(12) United States Patent
Wasnik et al.

(10) Patent No.: US 10,162,936 B2
(45) Date of Patent: Dec. 25, 2018

(54) SECURE REAL-TIME HEALTHCARE INFORMATION STREAMING

(71) Applicants: Pankaj Wasnik, Maharashtra (IN); Vipin Namboodiri, Karnataka (IN); Boppana Visweswara Rao, Bangalore (IN)

(72) Inventors: Pankaj Wasnik, Maharashtra (IN); Vipin Namboodiri, Karnataka (IN); Boppana Visweswara Rao, Bangalore (IN)

(73) Assignee: Ricoh Company, Ltd., Tokyo (JP)

( * ) Notice: Subject to any disclaimer, the term of this patent is extended or adjusted under 35 U.S.C. 154(b) by 222 days.

(21) Appl. No.: 15/067,059

(22) Filed: Mar. 10, 2016

(65) Prior Publication Data

US 2017/0262582 A1 Sep. 14, 2017

(51) Int. Cl.
*H04L 29/06* (2006.01)
*G06F 19/00* (2018.01)
*H04N 21/2343* (2011.01)
*H04N 21/2387* (2011.01)
*H04N 21/433* (2011.01)
*H04N 21/6587* (2011.01)
*H04N 21/845* (2011.01)

(52) U.S. Cl.
CPC ........ *G06F 19/321* (2013.01); *H04L 65/4069* (2013.01); *H04L 65/607* (2013.01); *H04N 21/2387* (2013.01); *H04N 21/23439* (2013.01); *H04N 21/234363* (2013.01); *H04N 21/4333* (2013.01); *H04N 21/6587* (2013.01); *H04N 21/8455* (2013.01)

(58) Field of Classification Search
CPC . G06F 19/321; H04L 65/4069; H04L 65/607; H04N 21/234363; H04N 21/23439; H04N 21/2387; H04N 21/4333; H04N 21/6587; H04N 21/8455
See application file for complete search history.

(56) References Cited

U.S. PATENT DOCUMENTS 5,926,611 A * 7/1999 Yang ................. G09B 5/065
375/240.1
6,937,273 B1 8/2005 Loui
(Continued)

FOREIGN PATENT DOCUMENTS

EP 0967796 12/1999
JP 2001-128144 5/2001
(Continued)

OTHER PUBLICATIONS

European Search Report from EP Application No. 17 154 938.9 dated Mar. 6, 2017, 10 pages.
(Continued)

*Primary Examiner* — Alina A Boutah
(74) *Attorney, Agent, or Firm* — Patent Law Works LLP

(57) ABSTRACT

A method includes transmitting a low-resolution stream, buffering a high-resolution stream in a buffer memory, receiving a request for a high-resolution media item, retrieving the high-resolution media item from the buffer memory based on the frame numbers, and transmitting the high-resolution media item. The request includes one or more frame numbers based on the low-resolution stream.

20 Claims, 6 Drawing Sheets

(56) References Cited

U.S. PATENT DOCUMENTS

| | | | |
|---|---|---|---|
| 7,197,070 B1* | 3/2007 | Zhang | H04B 1/66 375/240.01 |
| 7,590,550 B2 | 9/2009 | Schoenberg | |
| 2003/0142872 A1* | 7/2003 | Koyanagi | H04N 21/234327 382/236 |
| 2004/0218099 A1* | 11/2004 | Washington | H04N 5/77 348/571 |
| 2006/0050785 A1* | 3/2006 | Watanabe | H04N 7/17318 375/240.03 |
| 2008/0094427 A1* | 4/2008 | Debonnet | G09G 5/008 345/698 |
| 2008/0252778 A1* | 10/2008 | Dunki-Jacobs | G09G 5/00 348/441 |
| 2009/0097770 A1* | 4/2009 | Eppolito | G11B 27/034 382/256 |
| 2009/0219387 A1* | 9/2009 | Marman | G08B 13/19652 348/143 |
| 2010/0050221 A1* | 2/2010 | McCutchen | H04N 7/165 725/109 |
| 2010/0333155 A1* | 12/2010 | Royall | H04N 5/23203 725/105 |
| 2011/0283008 A1* | 11/2011 | Smelyansky | G09B 5/065 709/231 |
| 2013/0031589 A1* | 1/2013 | Casanova | H04N 21/234318 725/93 |
| 2013/0222583 A1 | 8/2013 | Earnshaw | |
| 2014/0019631 A1* | 1/2014 | Namboodiri | H04L 65/60 709/231 |
| 2016/0164938 A1* | 6/2016 | Yu | H04L 65/605 709/231 |
| 2016/0330374 A1* | 11/2016 | Ilic | H04N 5/23251 |
| 2017/0208328 A1* | 7/2017 | Kuusela | H04N 19/124 |

FOREIGN PATENT DOCUMENTS

| | | |
|---|---|---|
| JP | 2008-199677 | 8/2008 |
| WO | WO 2011120204 | 6/2011 |

OTHER PUBLICATIONS

Office Action from Japanese Patent Application No. 2017-023806, dated Jan. 16, 2018, 6 pgs.

* cited by examiner

SECURE REAL-TIME HEALTHCARE INFORMATION STREAMING

BACKGROUND

1. Field of the Invention

The present disclosure relates to an information streaming system. In particular, the present disclosure relates to streaming information over a constrained bandwidth network. Still more particularly, the present disclosure relates to streaming healthcare information.

2. Description of the Background Art

Remote healthcare, and in particular telehealth is an emerging area of contemporary healthcare. Telehealth is the delivery of health-related services and information via telecommunications technologies. Telehealth may allow a patient to be monitored between physician office visits which can improve patient health. Telehealth may also allow patients to access expertise which is not available in their local area. Telehealth could be as simple as two health professionals discussing a case over the telephone or as sophisticated as doing robotic surgery between facilities at different ends of the globe.

With the advent and wide adoption of the Internet, users in some parts of the world have seen a marked increase in networking capabilities including increased bandwidth. Additionally, advances in personal computers coupled with the advances in computer networking, have generally made streaming media practical and affordable for many people around the world. Other areas of the world have suffered from a digital divide where Internet connectivity has lagged. This digital divide is often times particularly evident in rural areas and developing countries.

SUMMARY

The present disclosure relates to information streaming. According to one innovative aspect of the subject matter in this disclosure, a method includes transmitting a low-resolution stream, buffering a high-resolution stream in a buffer memory, receiving a request for a high-resolution media item, retrieving the high-resolution media item from the buffer memory based on the frame numbers, and transmitting the high-resolution media item. The request for a high-resolution media item may include one or more frame numbers based on the low-resolution stream.

In general, another innovative aspect of the subject matter described in this disclosure, a method includes receiving a low-resolution stream, transmitting a request for a high-resolution media item, and receiving the high-resolution media item based on the frame numbers. The request for a high-resolution media item may include one or more frame numbers based on the low-resolution stream.

Other implementations of one or more of these aspects include corresponding systems, apparatuses, and computer program products, configured to perform the actions of the methods, encoded on computer storage devices.

It should be understood that language used in the present disclosure has been principally selected for readability and instructional purposes, and not to limit the scope of the subject matter disclosed herein.

BRIEF DESCRIPTION OF THE DRAWINGS

The present disclosure is illustrated by way of example, and not by way of limitation in the figures of the accompanying drawings in which like reference numerals are used to refer to similar elements.

DETAILED DESCRIPTION

Telehealth uses a robust data streaming infrastructure to stream various types of data used in diagnosis by remote medical specialist. The type of information streamed may include various media types including audio, video, text, etc. The type and information output of medical devices may dictate the type of information to be streamed. For example, an otoscope may stream video, whereas a stethoscope may stream audio. Other devices may include other types of media streams including text, three-dimensional environments, etc. Due to regulatory and personal privacy concerns, an effective streaming system for telehealth networks may also include authentication, encryption, and the ability to dynamically adapt to variations in an underlying network.

The disclosed technology provides a stream with a low-bit rate preview stream and the ability to provide a higher quality media item reflective of the low-bit rate preview stream in near real-time. As used herein, the low-bit rate preview stream may also be referred to as a low-resolution stream, a low-bandwidth stream, or the like. Generally, the low-bit rate preview stream may have a lower quality resolution and/or consume less bandwidth than a high-bit rate stream (alternatively referred to as high-resolution stream, high-bandwidth stream, or the like). Thus, in one use, at a high level, a doctor (or multiple doctors) may stream medical information with the low-bit rate preview stream, and when an area of particular interest arises in the low-bit rate preview stream, the doctor may indicate via a user interface that a higher quality media item should be grabbed that is based on the low-bit rate preview stream. For example, with a video stream, the low-bit rate preview stream may include timestamps or frame numbers aligned with a high-bit rate stream. The high-bit rate stream may not be transmitted to the doctor until it is requested and then only a portion or subset of the high-bit rate stream may be transmitted (e.g., the higher quality media item). For example, the higher quality media item may include a single frame or a series of frames of fixed length, thereby effectively lowering bandwidth usage. The higher quality media item may be extracted from the high-bit rate stream based on timestamps, frames numbers, etc., sent with the request to for the higher quality media item. Additionally, in some examples, while the higher quality media item is being transmitted, the low-bit rate stream may be paused or the bit-rate of the low-bit rate stream may be lowered even further.

Figure 1:
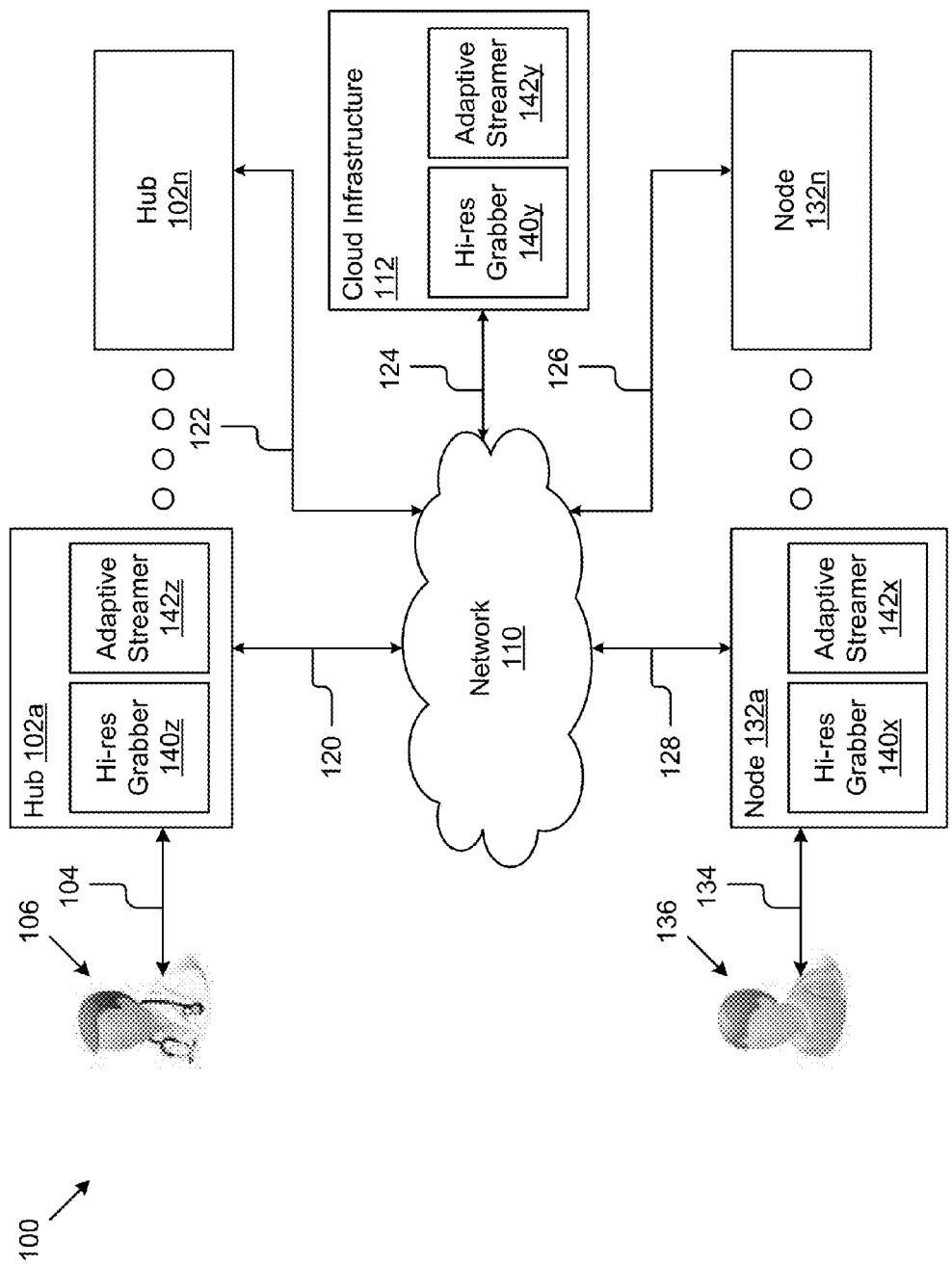
FIG. 1 depicts a high-level block diagram illustrating an example system for implementing information streaming according to the techniques described herein.

FIG. 1 depicts a high-level block diagram illustrating an example system 100 for implementing information streaming. The system includes one or more hubs 102, a cloud infrastructure 112, and one or more nodes 132 communicatively connected through a network 110. Thus, in the illustrated embodiment, the hub 102a, a cloud infrastructure 112, and the node 132a are communicatively coupled via signal lines 120, 124, and 128 to the network 110. Further, other hubs and nodes, such as hub 102n and node 132n, may be communicatively coupled to the network via signal lines 122 and 126. However, the present disclosure is not limited to this configuration and a variety of different system environments and configurations can be deployed and are within the scope of the present disclosure. Other embodiments may include additional or fewer components. For example, the cloud infrastructure 112 may include multiple instances located various remote locations.

These implementations are particularly advantageous in a number of respects. For instance, the technology described herein adaptively adjusts streaming with variations in the network bandwidth. Further, the technology provides effective utilization of scarce resources in low bandwidth situations.

It should be recognized that FIG. 1 as well as the other figures used to illustrate an embodiment including a letter after a reference number or numeral, for example, "102a" is a specific reference to the element or component that is designated by that particular reference numeral. In the event a reference numeral appears in the text without a letter following it, for example, "102," it should be recognized that such is a general reference to different embodiments of the element or component bearing that general reference numeral.

The hub 102 includes facilities used (as indicated by use line 104) by a doctor 106, or another healthcare provider who may diagnose patients and provide medical care. In particular, the hub 102 may implement, in part, information streaming. The hub 102 may include computing hardware, input devices, display devices, and other output devices. The hub 102, may include a non-transitory computer-usable (e.g., readable, writeable, etc.) medium, which can be any non-transitory apparatus or device that can contain, or store data, computer programs, software, code routines, etc., for processing by or in connection with a processor. The hub 102 may also include various applications. For instance, the hub 102 may include a high-resolution grabber 140z and an adaptive streamer 142z. Information detailing the high-resolution grabber 140z and the adaptive streamer 142z are described further with reference to FIGS. 2 and 3, and the remaining figures.

The network 110 can be a conventional type, wired or wireless, and may have numerous different configurations including a star configuration, token ring configuration or other configurations. Furthermore, the network 110 may include a wide area network (WAN) (e.g., the Internet), a local area network (LAN), and/or other interconnected data paths across which multiple devices may communicate. In some embodiments, the network 110 may be a peer-to-peer network. The network 110 may also be coupled to or includes portions of a telecommunications network for sending data in a variety of different communication protocols. In some embodiments, the network 110 may be a VPN operating over one of the aforementioned types of networks.

The cloud infrastructure 112 may be an Internet, or other network-based, computing platform that provides processing resources and data storage for information streaming and stream auditing. In particular, the cloud infrastructure may implement, in part, information streaming. The cloud infrastructure 112 may include computing hardware, input devices, display devices and other output devices. The cloud infrastructure 112, may include a non-transitory computer-usable (e.g., readable, writeable, etc.) medium, which can be any non-transitory apparatus or device that can contain, or store data, computer programs, software, code routines, etc., for processing by or in connection with a processor. The cloud infrastructure 112 may also include various applications. For instance, the cloud infrastructure 112 may include a high-resolution grabber 140y and an adaptive streamer 142y. Information detailing the high-resolution grabber 140y and the adaptive streamer 142y are described further with reference to FIGS. 2 and 3, and the remaining figures.

The node 132 includes facilities used (as indicated by use line 134) by a patient and/or a technician 136 to receive telehealth medical care. A technician may physically attend to the patient and perform duties such as taking the patient's vitals, and technically assisting the patient in receiving the telehealth medical care through the system 100. The node 132 may implement, in part, information streaming. The node 132 may include computing hardware, input devices, display devices and other output devices. The node 132, may include a non-transitory computer-usable (e.g., readable, writeable, etc.) medium, which can be any non-transitory apparatus or device that can contain, or store data, computer programs, software, code routines, etc., for processing by or in connection with a processor. The node 132 may also include various applications. For instance, the node 132 may include a high-resolution grabber 140x and an adaptive streamer 142x. Information detailing the high-resolution grabber 140x and the adaptive streamer 142x are described further with reference to FIGS. 2 and 3, and the remaining figures.

The doctor 106 may select a remote medical device to manipulate from an application on the hub 102. In some cases, the application may be web application accessed through a web browser and hosted by a web server. Regardless, when a remote medical device is manipulated in the application, a message may be sent to the node 132 for executing manipulation of a locally attached medical device. Thus, the locally attached medical device functionally embodies the remote medical device referenced in the application. In some cases, the locally attached medical device may produce a device stream. For example, an otoscope may produce a video device stream. A stethoscope may produce an audio device stream. A magnetic resonance imaging (MRI) scanner may produce an image. A camera may produce a video and a microphone may produce audio signals to interact with the patient 136 through.

In some cases, the message may be transferred using a Real Time Messaging Protocol (RTMP) and may pass through the cloud infrastructure for audit recording. The telemedicine system 100 may be used in some cases to facilitate communication between the hub 102, the cloud infrastructure 112, and the node 132. In some cases, the cloud infrastructure may implement load balancing to spread utilization of computing resources across multiple servers, sites, and locales.

Figure 2:
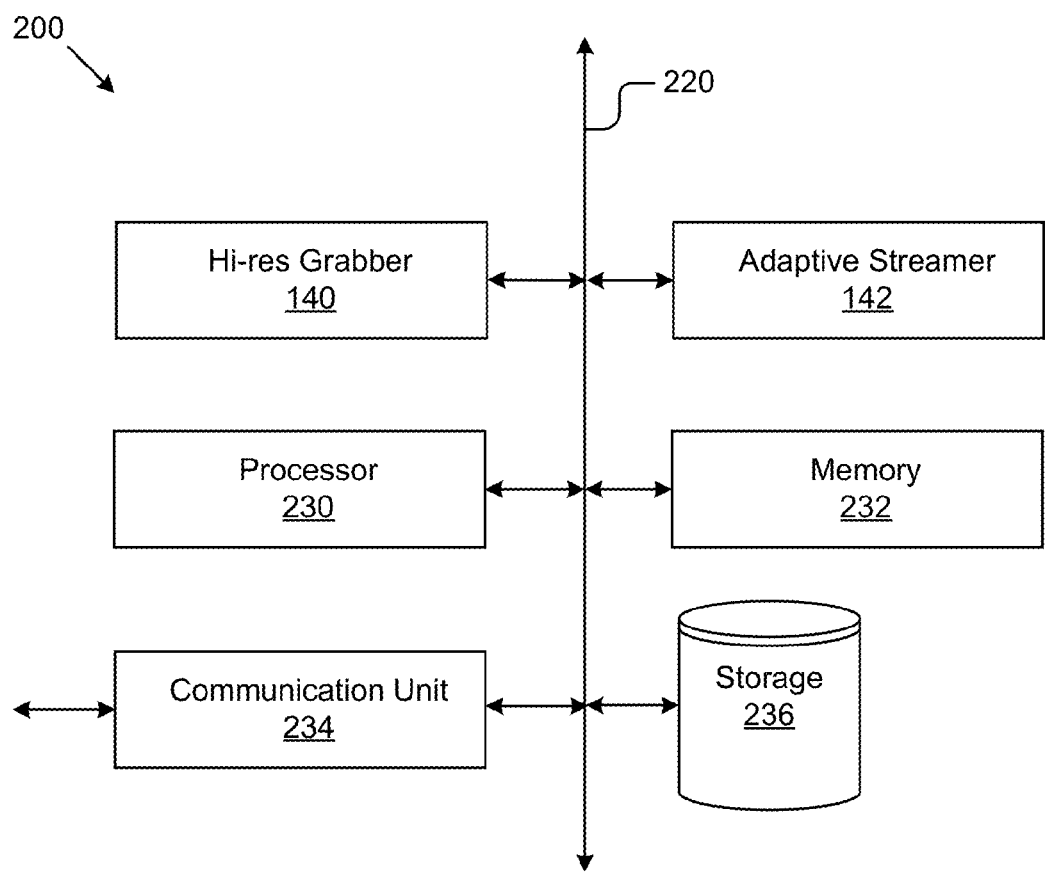
FIG. 2 depicts a block diagram illustrating an example of a computing device for implementing information streaming according to the techniques described herein.

FIG. 2 depicts a block diagram illustrating an example of a computing device 200 for implementing information streaming. The computing device 200 includes a high-resolution grabber 140, an adaptive streamer 142, a processor 230, a memory 232, a communication unit 234, and storage 236. The components of the computing device 200 are communicatively coupled by a bus 220. In some embodiments the hub 102, the cloud infrastructure 112, and/or the node 132 may include the computing device 200.

The processor 230 includes an arithmetic logic unit, a microprocessor, a general purpose controller or some other processor array to perform computations and provide electronic display signals to a display device. The processor 230 is coupled to the bus 220 for communication with the other components of the system 200. Although FIG. 2 depicts a single processor 230, multiple processors or processing cores may be included. Other processors, operating systems, sensors, displays and physical configurations are possible.

The memory 232 stores instructions and/or data that may be executed by the processor 230. The memory 232 is coupled to the bus 220 for communication with the other components of the system 220. The instructions and/or data may include code for performing the techniques described herein. The memory 232 may be a dynamic random access memory (DRAM) device, a static random access memory (SRAM) device, flash memory or some other memory device. In some embodiments, the memory 232 also includes a non-volatile memory or similar permanent storage device and media including a hard disk drive, a floppy disk drive, a CD ROM device, a DVD ROM device, a DVD RAM device, a DVD RW device, a flash memory device, or some other mass storage device for storing information on a more permanent basis.

The communication unit 234 transmits and receives data to and from the network 110. The communication unit 234 is coupled to the bus 220. In some embodiments, the communication unit 234 includes a port for direct physical connection to the network 110 or to another communication channel. In some embodiments, the communication unit 234 includes a wireless transceiver for exchanging data with the network 110 or other communication channels using one or more wireless communication methods, including IEEE 802.11, IEEE 802.16, BLUETOOTH®, cellular communication, or another suitable wireless communication method.

The storage 236 can be a non-transitory memory that stores data for providing the functionality described herein. The storage 236 may be a dynamic random access memory (DRAM) device, a static random access memory (SRAM) device, flash memory or some other memory devices. In some embodiments, the storage 236 also includes a non-volatile memory or similar permanent storage device and media including a hard disk drive, a floppy disk drive, a CD ROM device, a DVD ROM device, a DVD RAM device, a DVD RW device, a flash memory device, or some other mass storage device for storing information on a more permanent basis.

The high-resolution grabber 140 can be software including routines for implementing information streaming. In some embodiments, the high-resolution grabber 140 can be set of instructions executable by the processor 230 to provide functionality described below for streaming medical information. In some other embodiments, the high-resolution grabber 140 may be stored in the memory 232 of the computing device 200 and can be accessible and executable by the processor 230. The high-resolution grabber 140 may be adapted for cooperation and communication with the processor 230 and other components of the computing device 200 via the bus 220. In some cases, the functionality of the high-resolution grabber 140 may be split between the hub 102 (e.g., high-resolution grabber 140z), the cloud infrastructure 112 (e.g., high-resolution grabber 140y), and the node 132 (e.g., the high-resolution grabber 140x).

As an illustrative example, the high-resolution grabber 140 may be used in streaming videos. The high-resolution grabber 140 may allow the doctor 106 to grab a high quality frame corresponding to a frame of a low-bit rate preview stream. This high quality frame may be used by the doctor to perform a diagnosis while the low-bit rate preview stream of the patient 136 continues.

With the high-resolution grabber 140, uplink bandwidth may be preserved since there may not be the need to send high quality video for the entire duration of the interaction between the doctor 106 and the patient and/or technician 136. By viewing the low quality preview video, the doctor 106 may be able to identify frames of interest and request corresponding high-quality frames to be sent so that the doctor 106 can provide a more accurate diagnosis based on the additional information included in the high-quality frames.

In one implementation, the doctor 106 may pause the low-bit rate preview stream whenever he identifies a frame of interest. The pausing of the low-resolution stream may send a pause command from the hub 102 to the node 132 along with the frame of interest's timestamp or frame number. The node 132 may fetch the corresponding frame based on the provided frame number from a high-resolution locally streamed video. The node 132 may save the frame locally and upon receiving a download request from the doctor 106 through the hub 102 may upload the high-resolution frame to the hub 102. The hub 102 may then display or otherwise make available the high-resolution frame to the doctor 106.

In some cases, the high-resolution stream may be locally streamed or buffered to the memory 232 instead of saving and maintaining it on the storage device 236. This maintains patient confidentiality as the stream is not save to persistent storage. In some examples, the high-resolution stream may be transcoded from a device stream to a network stream prior to buffering the high-resolution stream to the memory 232. The high-resolution grabber 140 is discussed in further detail with reference to FIG. 3 and the remaining figures.

The adaptive streamer 142 can be software including routines for implementing information streaming techniques as described herein. In some embodiments, the adaptive streamer 142 can be set of instructions executable by the processor 230 to provide functionality described below for streaming medical information. In some other embodiments, the adaptive streamer 142 may be stored in the memory 232 of the computing device 200 and can be accessible and executable by the processor 230. The adaptive streamer 142 may be adapted for cooperation and communication with the processor 230 and other components of the computing device 200 via the bus 220. In some cases, the functionality of the adaptive streamer 142 may be split between the hub 102 (e.g., adaptive streamer 142z), the cloud infrastructure 112 (e.g., adaptive streamer 142y), and the node 132 (e.g., the adaptive streamer 142x).

The adaptive streamer 142 may provide authentication and authorization to access the system 100. For example, the adaptive streamer 142 may use token based authentication. Thus, streaming of information with the system 100 may be limited to cases where both of the parties (e.g., the doctor 106 and the patient 136) have been successfully authenticated. Additionally, the adaptive streamer 142 may provide encryption to information streams. For example, audio, visual, and text data may be protected by high-bandwidth digital content protection (HDCP) and/or cryptographic techniques.

The adaptive streamer 142 may include logic to stream data suited to available network bandwidth in order to avoid playback streaming issues at the hub 102. Playback streaming issues may occur in-part because of network bandwidth variations. Thus, to smooth out the network bandwidth variations, the adaptive streamer 142 may provide auto-forward functionality to send pending data as soon as the available network bandwidth reaches a threshold. Further, the adaptive streamer 142 may provide bitrate modification to match the available bandwidth. Additionally, the adaptive streamer 142 may provide a secure connection interface such as secure hypertext transfer protocol (HTTPS) to transfer data within the system 100. In some cases, transfer of data may include a push mechanism such as secure server-sent events (SSE) implemented in many modern web browsers.

Figure 3:
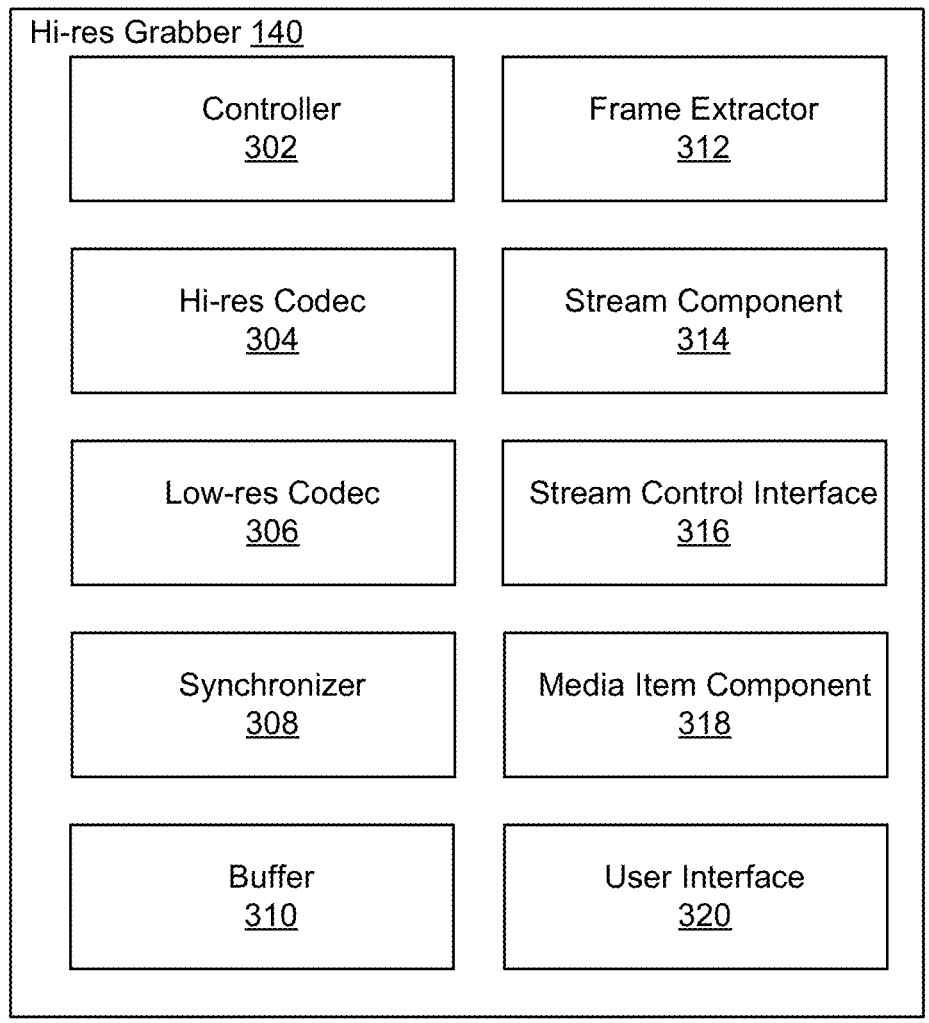
FIG. 3 depicts a block diagram illustrating an example of a high-resolution grabber according to the techniques described herein.

FIG. 3 depicts a block diagram illustrating an example of a high-resolution grabber 140. The high-resolution grabber 140 includes a controller 302, a high-resolution codec 304, a low-resolution codec 306, a synchronizer 308, a buffer 310, a frame extractor 312, a stream component 314, a stream control interface 316, a media item component 318, and a user interface 320. These components of the high-resolution grabber 140 are communicatively coupled to each other, for example, via the bus 220.

The controller 302 can be software including routines for handling communications between the high-resolution grabber 140 and other components of the computing device 200. In some embodiments, the controller 302 can be a set of instructions executable by the processor 230 to provide the functionality described below for handling communications between the high-resolution grabber 140 and other components of the computing device 200. In some other embodiments, the controller 302 can be stored in the memory 232 of the computing device 200 and can be accessible and executable by the processor 230. The controller 302 may be adapted for cooperation and communication with the processor 230 and other components of the computing device 200 via the bus 220.

The controller 302 sends and receives data, via the communication unit 234, to and from the hub 102, the cloud infrastructure 112, and/or the node 132. For example, the controller 302 receives from the node 132, via the communication unit 234, a low-bit rate preview stream and a high-resolution media item. In some examples, the controller 302 may communicate with the user interface 320 to present the received low-bit rate preview stream and high-resolution media item to the user on a display. Further the controller may receive requests from the user interface 320 requesting specific frames of interest or requesting to pause or restart streams.

In some embodiments, the controller 302 receives data from the high-resolution codec 304 and/or and sends the data to components of the high-resolution grabber 140. For example, the controller 302 may receive a high-resolution encoded stream from the high-resolution codec 304 and communicate the high-resolution encoded stream to the buffer 310 for temporary storage. In some embodiments, the controller 302 receives data from the low-resolution codec 306 and/or sends the data to components of the high-resolution grabber 140. For example, the controller 302 may receive a low-resolution encoded stream from the low-resolution codec 306 and communicate the low-resolution encoded stream to the stream component 314 for transmission of the stream. In some embodiments, the controller 302 may communicate with the synchronizer 308 to request synchronized frame numbers between the high-resolution stream temporarily stored in the buffer 310 and the low-bit rate preview stream received from the low-resolution codec 306.

The high-resolution codec 304 can be software including routines for transforming a device stream into a high-resolution stream. In some embodiments, the high-resolution codec 304 can be a set of instructions executable by the processor 230 to provide functionality described below for digitizing a device stream and applying a stream compression to the digitized device stream. In this particular case, the stream compression may be biased towards a more high quality stream rather than a lower bit-rate that would consume less bandwidth when transmitted over the network 110. For example, the high-resolution codec 304 may receive an analog video device stream from a device driver. The high-resolution codec 304 may sample the analog video device stream at a particular frequency to create a digital frame rate and may further sample each frame with a window size to transform each analog frame to a digital frame. Further, a modern video compression algorithm such as H.264 or high efficiency video coding (HEVC, also known as H.265) may be applied to the digitized video device stream to generate a high-resolution stream. The high-resolution codec 304 may then forward the high-resolution stream to the buffer 310 for temporary storage.

The low-resolution codec 306 can be software including routines for transforming a device stream into a low-bit rate preview stream. In some embodiments, the low-resolution codec 306 can be a set of instructions executable by the processor 230 to provide functionality described below for digitizing a device stream and applying a stream compression to the digitized device stream. In this particular case, the stream compression may be biased towards a lower bit-rate that would consume less bandwidth when transmitted over the network 110 rather than producing a high-resolution stream. For example, the low-resolution codec 306 may receive an analog video device stream from a device driver. The low-resolution codec 306 may sample the analog video device stream at a particular frequency to create a digital frame rate and may further sample each frame with a window size to transform each analog frame to a digital frame. Further, a modern video compression algorithm such as H.264 or high efficiency video coding (HEVC, also known as H.265) may be applied to the digitized video device stream to generate a low-bit rate preview stream.

The low-resolution codec 306 may then forward the low-bit rate preview stream to the stream component 314 for transmission to the hub 102 and/or node 132. In one embodiment, the stream component 314 may be part of high-resolution grabber 140y such that the low-bit rate preview stream and the high resolution stream are transmitted to the hub 102 via the cloud infrastructure 112. This allows for additional access control (e.g., the identity of a doctor 106 at the hub 102 may be authenticated before the streamed data is presented at the hub 102). Additionally, transmitting the low-bit rate preview stream and the high resolution stream via the cloud infrastructure 112 provides efficient one-to-many streaming capability allowing multiple healthcare professionals to view the same streamed content concurrently. Streaming through the could infrastructure 112 also allows for better control of the quality of service provided to the hub 102.

The synchronizer 308 can be software including routines for identifying frames or timestamps in the low-bit rate preview stream (e.g., transmitted via the stream component 314) and the high-resolution stream (e.g., stored in buffer 310) that synchronize the two streams to the same relative time. In some embodiments the synchronizer 308 can be stored in the memory 232 of the computing device 200 and can be accessible and executable by the processor 230. The synchronizer 308 may be adapted for cooperation and communication with the processor 330 and other components of the computing device 200 via the bus 220.

The buffer 310 may be a portion of memory 232 for temporarily storing data for a stream. In some embodiments, the buffer 310 can temporarily store data from a stream for a fixed duration of time. For example the buffer 310 may store data for a high-resolution stream for the previous few minutes. In some embodiments the buffer 310 can be stored in the memory 232 of the computing device 200 and can be accessible by the processor 230. The buffer 310 may be adapted for cooperation and communication with the processor 230 and other components of the computing device 200 via the bus 220.

The frame extractor 312 can be software including routines for extracting media items from the high-resolution stream temporarily stored in the buffer 310. In some embodiments, the frame extractor 312 can be a set of instructions executable by the processor 230 to provide functionality described below for locating the media item within the buffer 310, copying the media item, and transmitting the media item through the media item component 318 to the node 132. In some embodiments, the frame extractor 312 can be stored in the memory 232 of the computing device 200 and can be accessible and executable by the processor 230. The frame extractor 312 may be adapted for cooperation and communication with the processor 230 and other components of the computing device 200 via the bus 220.

The stream component 314 can be software including routines for publishing streams. In some embodiments, the stream component 314 can be a set of instructions executable by the processor 230 to provide functionality described below for formatting a stream for publication over the network 110. For example, the stream component 314 may transmit the low-resolution stream over the network 110 from the node 132 to the hub 102. In some embodiments the stream component 314 can be stored in the memory 232 of the computing device 104 and can be accessible and executable by the processor 230. The stream component 314 may be adapted for cooperation and communication with the processor 230 and other components of the computing device 200 via the bus 220.

The stream control interface 316 can be software including routines for controlling a stream and requesting high-resolution media items. In some embodiments, the stream control interface 316 can be a set of instructions executable by the processor 230 to provide functionality described below for receiving and processing stream control messages. For example, the stream control interface 316 may receive a stream control message to halt streaming the low-resolution stream. The stream control interface 316 may communicate with the stream component 314 to halt transmission of the low-resolution stream. Further, the stream control interface 316 may receive a stream control message to retrieve a high-resolution media item based on frame numbers or time stamps included in the stream control message. The stream control interface 316 may communicate with the media item component 318 to retrieve the specified high-resolution media item. In some embodiments the stream control interface 316 can be stored in the memory 232 of the computing device 200 and can be accessible and executable by the processor 230. The stream control interface 316 may be adapted for cooperation and communication with the processor 230 and other components of the computing device 200 via the bus 220.

The media item component 318 can be software including routines for extracting data from the buffer 310. In some embodiments, the media item component 318 can be a set of instructions executable by the processor 230 to provide functionality described below for communicating with the synchronizer 308 to identify data in the buffer 310 to extract and format as a high-resolution media item. In some embodiments the media item component 318 can be stored in the memory 232 of the computing device 200 and can be accessible and executable by the processor 230. The media item component 318 may be adapted for cooperation and communication with the processor 230 and other components of the computing device 200 via the bus 220.

Figure 6:
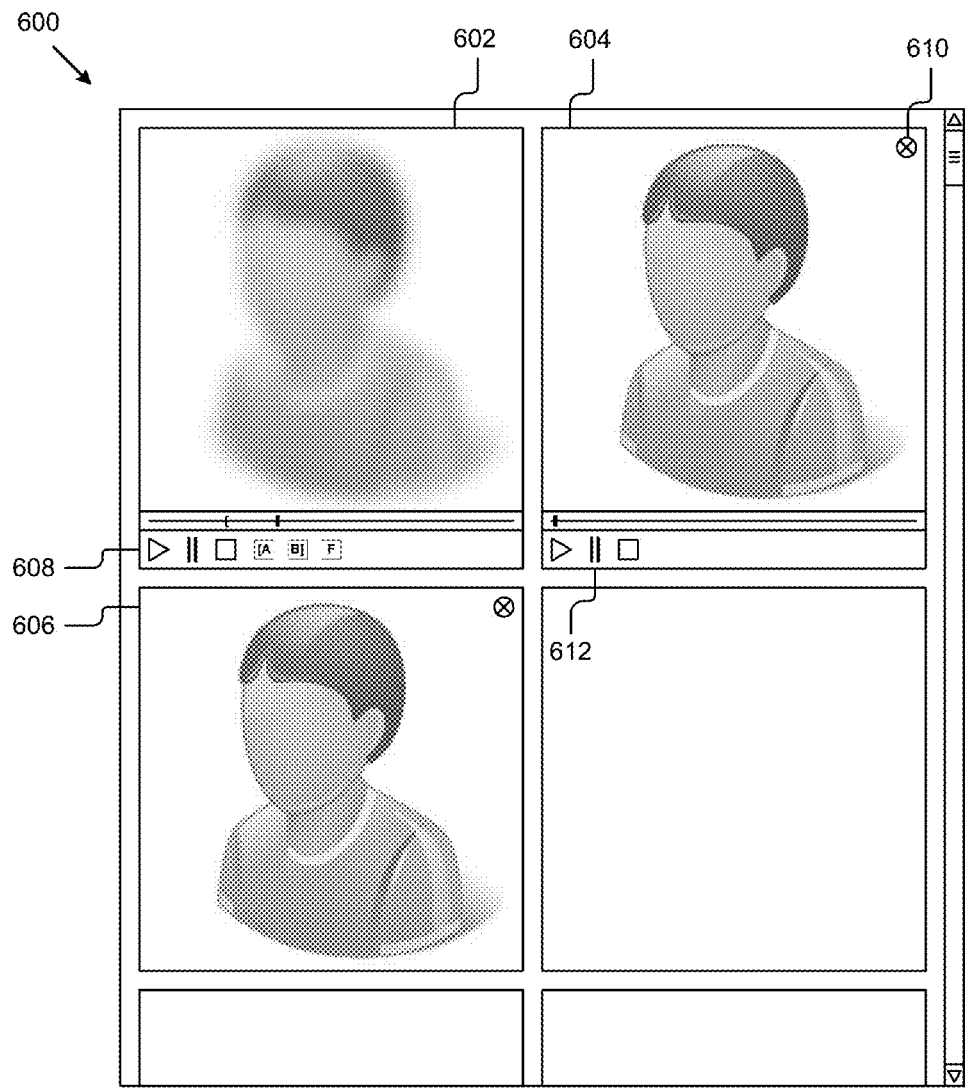
FIG. 6 depicts schematic diagram illustrating an example graphical user interface according to the techniques described herein.

In some embodiments, the user interface 320 receives, from the high-resolution grabber 140, a stream or media component to display. In some embodiments, the user interface 320 receives, from the stream component 314 or the media item component 318 across the network 110 an information stream or media item to present to the user. For example, the high-resolution grabber 140z may receive a low-resolution stream from the stream component 314 of high-resolution grabber 140x. As another example, the high-resolution grabber 140z may receive a high-resolution media item from the high-resolution grabber 140x. Examples of a graphical user interface are shown in FIG. 6.

Figure 4:
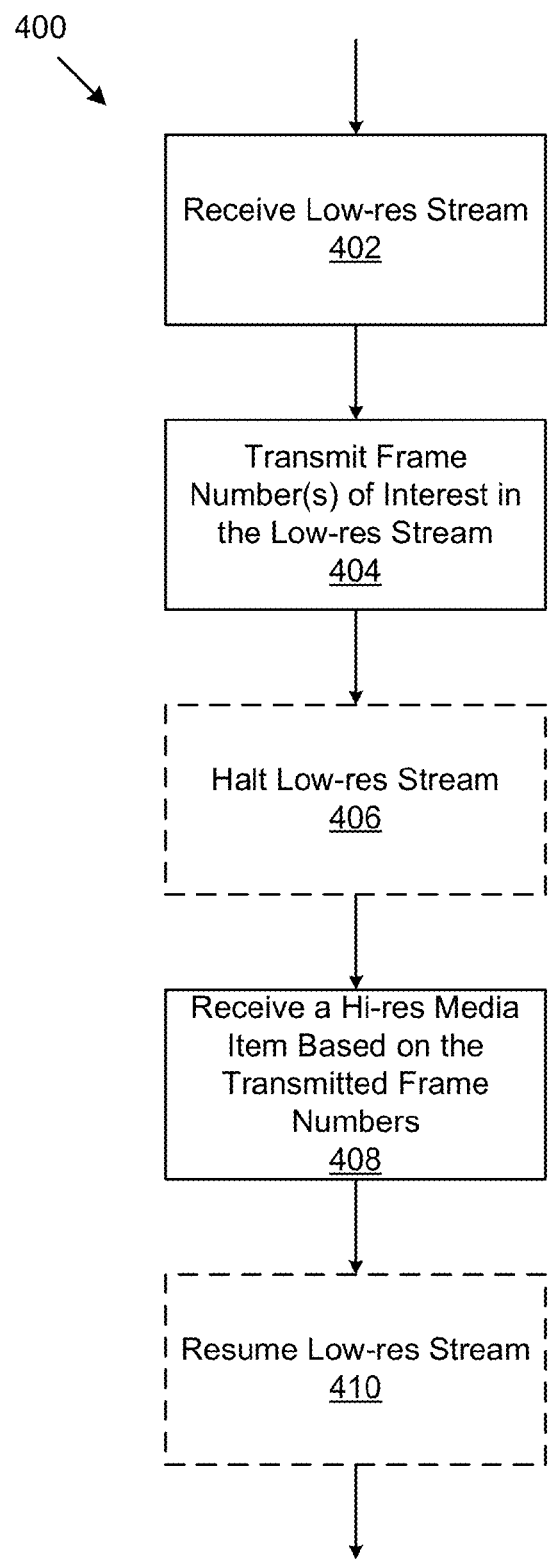
FIG. 4 depicts a flow chart of an example method of information streaming according to the techniques described herein.

FIG. 4 depicts a flow chart of an example method of information streaming 400. The method 400 may begin by receiving a low-resolution stream 402. For example, the high-resolution grabber 140x, may transmit a low-resolution stream to the high-resolution grabber 140z. Thus, the node 132a may transmit the low-resolution preview stream to the hub 102a so that the hub 102a receives 402 the low-resolution stream. In particular, the controller 302 may receive the low-resolution stream and communicate the low-resolution stream to the user interface 320. For example, the user interface 320 may play a video stream with a video player. The video player may include user interface controls that allow a user (e.g., the doctor 106) to specify frame numbers of interest in the low-resolution stream.

Accordingly, the high-resolution grabber 140z may transmit 404 a request for high-resolution media item along with one or more frame numbers of interest based on the low-resolution stream. For example, the user interface 320 may receive a user input to request a high-resolution copy of a given frame. The low-resolution stream may be playing and the user may simply interact with a user interface control to indicate such a request. The user interface 320 may then pass the frame number of interest to the stream control interface 316. The stream control interface 316 in the hub 102a may transmit this request to the high-resolution grabber 140x in node 132a using the network 110.

Optionally, the user interface 320 may transmit a request to halt 406 the low-resolution stream. This halting of the low-resolution stream may free up bandwidth to receive the high-resolution media item. For example, the user interface 320 may automatically transmit a request to halt the low-resolution stream in response to a user input indicating frame numbers of interest. The user interface 320 may communicate the request halt the low-resolution stream to the stream control interface 316 in the high-resolution grabber 140z on the hub 102a. The stream control interface may transmit this request to halt the low-resolution stream to the high-resolution grabber 140x in node 132a using the network 110.

The hub 102a may then receive 408 the high-resolution media item based on the transmitted frame numbers of interest in the low-resolution stream. For example, the controller 302 may receive a high-resolution media item from the high-resolution grabber 140x that is transmitted over the network 110. The controller 302 may then pass the high-resolution media item to the user interface 320 for display to, and interaction with, the user (e.g., doctor 106).

Optionally, the method 400 may further include transmitting, by the hub 102a) a request to resume 410 the low-resolution stream. In some cases, the request to resume the low-resolution stream is generated upon completion of receiving the high-resolution media item. For instance, when the controller 302 determines that the high-resolution media item has been completely downloaded, the controller 302 may communicate with stream control interface 316 to request resumption of the low-resolution stream. Thus, the high-resolution grabber 140z on the hub 102a may transmit a request to resume the low-resolution stream to the high-resolution grabber 140x on the node 132a.

Figure 5:
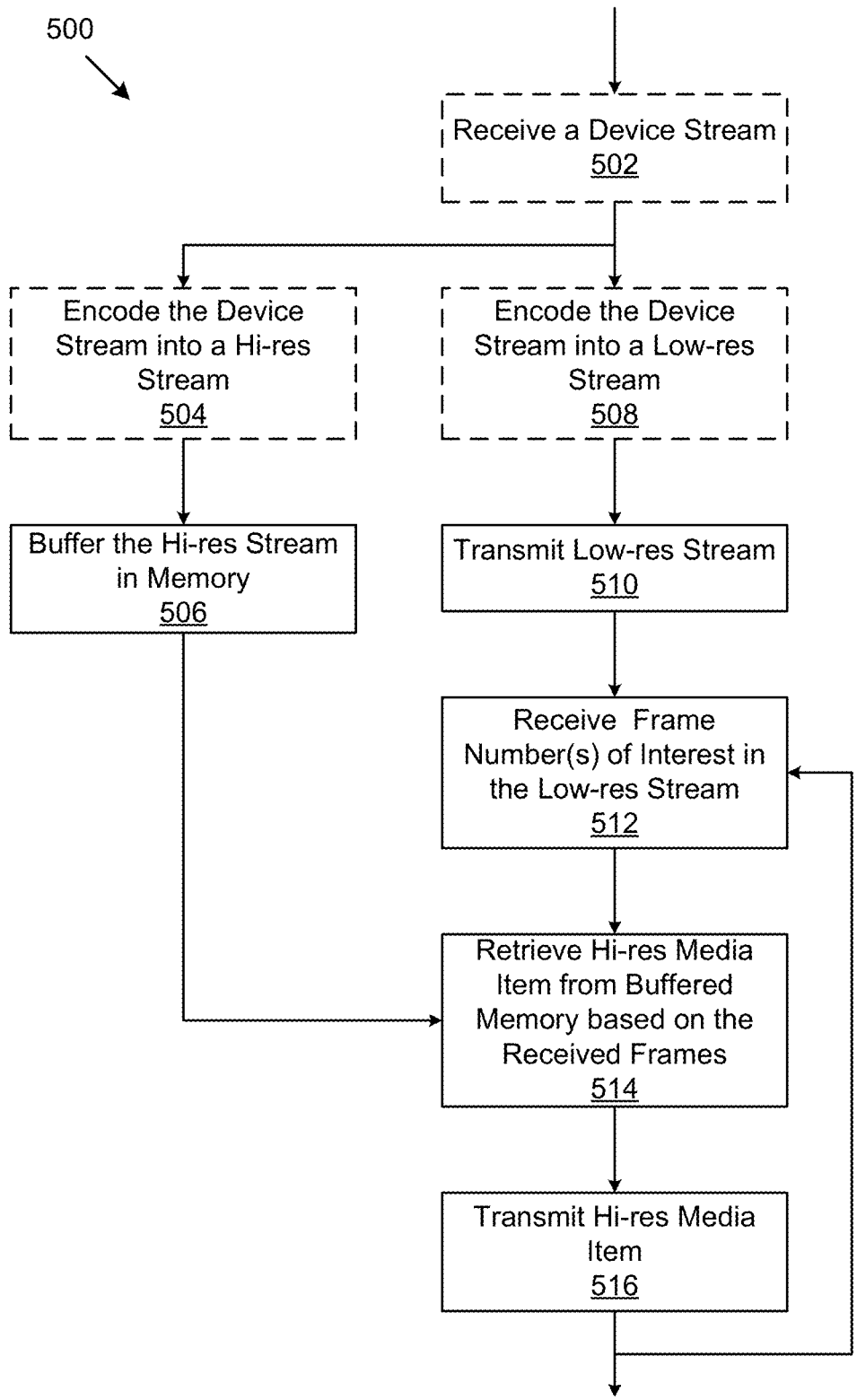
FIG. 5 depicts a flow chart of another example method of information streaming according to the techniques described herein.

FIG. 5 depicts a flow chart of another example method of information streaming 500. The method 500 may include receiving 502 a device stream. For example, the device stream may come from a hardware device connected directly to the node 132a through a device driver. As an example, the device may be a video camera for interacting with the patient 136. The high-resolution grabber 140x on the node 132a may optionally encode the device stream into a high-resolution stream 504 and a low-resolution stream 508. For instance, the controller 302 may interact with the device driver and receive 502 the device stream. In turn, the controller 302 may duplicate the device stream and communicate copies of the device stream to the high-resolution codec 304 and the low-resolution codec 306.

The high-resolution codec 304 may digitize the device stream and apply a compression algorithm and communicate the digitized and compressed stream to the buffer 310 to buffer 506 the high-resolution stream in memory 232. Similarly, the low-resolution codec 306 may digitize the device stream and apply a compression algorithm and communicate the digitized and compressed stream to the stream component to transmit 510 the low-resolution stream from the node 132a to the hub 102a across the network 110.

The node 132a receives 512 frame numbers of interest in the low-resolution stream. For example, high-resolution grabber 140z on the hub 102a may transmit frame numbers of interest across the network 110 to the high-resolution grabber 140x on the node 132a. The high-resolution grabber 140x, and in particular, the controller 302 may receive 512 the request for the high-resolution media item including the frame number of interest based on a low-resolution stream. The controller 302 may then request retrieval 514 of the high-resolution media item from the buffer 310 and ensure that the high-resolution media item is properly synchronized with the low-resolution stream by communicating with the synchronizer 308.

The high-resolution media item is transmitted 516 to the hub 102. For example, the high-resolution media item may be transmitted from the node 132 to the hub 102. Where the method 500 is ongoing, the method may then wait to receive 512 other frame numbers of interest in the low-resolution stream. When the low-resolution stream has ended, the method 512 may also end. It should be noted that like method 400, method 500 may include steps to halt transmission of the low-resolution stream and resume transmission of the low-resolution stream. In some cases, it may be desirable to halt transmission of the low-resolution stream after frame numbers of interest have been received 512 and before the high-resolution media item is transmitted 516 in order to effectively free up bandwidth. Likewise, resumption of the low-resolution stream may occur after transmitting 516 the high-resolution media item and receiving 512 new frames of interest. In some cases, this halting and resumption of the low-resolution stream may happen automatically in connection with the aforementioned steps of the method 500.

In some embodiments, the doctor 106 may control the high-resolution grabber 140z through slowing playback of the low-resolution stream. Additionally, the system 100 may pre-fetch high-resolution media items based on predictive algorithms of when the doctor 106 may be likely to request a high-resolution media item. Predictive algorithms may further factor in bandwidth constraints and an available bandwidth ceiling available at a given time.

It should be noted that while the high-resolution grabber 140z has been explained in terms of the hub 102 and the node 132 with reference to FIGS. 4 and 5, it should be appreciated that in some cases the cloud infrastructure 112 may play an equally important role in the implementation of information streaming. For instance, the high-resolution grabber 140y may encompass functionality of both upstream and downstream high-resolution grabbers. This may be particularly useful where bandwidth constraints are more prevalent between the hub 102 and the cloud infrastructure 112, or alternatively between the node 132 and the cloud infrastructure 112. As an illustrative example, the node 132 may be located at a community health center in a rural village, the cloud infrastructure may be located in a medium sized city near the village, and the hub may be located in a metropolitan city. In this case, the bandwidth constraints between the node 132 and the cloud infrastructure 112, and the bandwidth constraints between the hub and the cloud infrastructure may be significantly different. In some cases the buffering may occur within the cloud infrastructure's 112 high-resolution grabber 140y.

Additionally, the cloud infrastructure 112 may serve as a healthcare auditing service. Billing departments, insurance providers, and customer care may have limited authorized access to information retained in the cloud infrastructure 112.

FIG. 6 depicts a schematic diagram illustrating an example graphical user interface 600. In particular, graphical user interface 600 shows a low-resolution stream playing in a video player 602, a high-resolution media item that is a video ready for play in another video player 604, and a high-resolution media item that is a picture displayed in a frame 606. With the low-resolution stream video player 602, there are a set of user interface controls 608. For instance, the user interface controls 608 may include functions such as play, pause, and stop. Additionally, the user interface controls 608 may include additional functionality such as selecting the first frame, last frame, or selecting a single frame from the low-resolution stream playing in the video player 602. Similarly, with the high-resolution stream video player 604 there are a set of user interface controls 612. For instance, the user interface controls 612 may include functions such as play, pause, and stop. Additionally, high-resolution media items displayed in the user interface 600 may include a close control 610 to hide or dispose of high-resolution media items that the user has deemed are no longer of value to display. While the user interface depicted shows a high-resolution media item that is a video and another high-resolution media item that is a picture, it should be noted that the technology disclosed herein is not limited to those types of media. In some cases, the high-resolution media-item may be a three-dimensional graphic of a medical imaging scan. Thus, it should be further noted that the low-resolution stream is also not limited to the media types discussed above. As a non-limiting example, the low-resolution stream may include a medical imaging scan.

Systems and methods for implementing information streaming are described below. In the above description, for purposes of explanation, numerous specific details were set forth. It will be apparent, however, that the disclosed technologies can be practiced without any given subset of these specific details. In other embodiments, structures and devices are shown in block diagram form. For example, the disclosed technologies are described in some implementations above with reference to interfaces and particular hardware. Moreover, the technologies disclosed above primarily in the context of on line services; however, the disclosed technologies apply to other data sources and other data types (e.g., collections of other resources for example images, audio, web pages).

Reference in the specification to "one embodiment", "some embodiments" or "an embodiment" means that a particular feature, structure, or characteristic described in connection with the embodiment is included in at least one embodiment of the disclosed technologies. The appearances of the phrase "in one embodiment" in various places in the specification are not necessarily all referring to the same embodiment.

Some portions of the detailed descriptions above were presented in terms of processes and symbolic representations of operations on data bits within a computer memory. A process can generally be considered a self-consistent sequence of steps leading to a result. The steps may involve physical manipulations of physical quantities. These quantities take the form of electrical or magnetic signals capable of being stored, transferred, combined, compared, and otherwise manipulated. These signals may be referred to as being in the form of bits, values, elements, symbols, characters, terms, numbers, or the like.

These and similar terms can be associated with the appropriate physical quantities and can be considered labels applied to these quantities. Unless specifically stated otherwise as apparent from the prior discussion, it is appreciated that throughout the description, discussions utilizing terms for example "processing" or "computing" or "calculating" or "determining" or "displaying" or the like, may refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The disclosed technologies may also relate to an apparatus for performing the operations herein. This apparatus may be specially constructed for the required purposes, or it may include a general-purpose computer selectively activated or reconfigured by a computer program stored in the computer.

The disclosed technologies can take the form of an entirely hardware implementation, an entirely software implementation or an implementation containing both hardware and software elements. In some implementations, the technology is implemented in software, which includes but is not limited to firmware, resident software, microcode, etc.

Furthermore, the disclosed technologies can take the form of a computer program product accessible from a non-transitory computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

A computing system or data processing system suitable for storing and/or executing program code will include at least one processor (e.g., a hardware processor) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modems and Ethernet cards are just a few of the currently available types of network adapters.

Finally, the processes and displays presented herein may not be inherently related to any particular computer or other apparatus. Various general-purpose systems may be used with programs in accordance with the teachings herein, or it may prove convenient to construct a more specialized apparatus to perform the required method steps. The required structure for a variety of these systems will appear from the description below. In addition, the disclosed technologies were not described with reference to any particular programming language. It will be appreciated that a variety of programming languages may be used to implement the teachings of the technologies as described herein.

The foregoing description of the implementations of the present techniques and technologies has been presented for the purposes of illustration and description. It is not intended to be exhaustive or to limit the present techniques and technologies to the precise form disclosed. Many modifications and variations are possible in light of the above teaching. It is intended that the scope of the present techniques and technologies be limited not by this detailed description. The present techniques and technologies may be implemented in other specific forms without departing from the spirit or essential characteristics thereof. Likewise, the particular naming and division of the modules, routines, features, attributes, methodologies and other aspects are not mandatory or significant, and the mechanisms that implement the present techniques and technologies or its features may have different names, divisions and/or formats. Furthermore, the modules, routines, features, attributes, methodologies and other aspects of the present technology can be implemented as software, hardware, firmware or any combination of the three. Also, wherever a component, an example of which is a module, is implemented as software, the component can be implemented as a standalone program, as part of a larger program, as a plurality of separate programs, as a statically or dynamically linked library, as a kernel loadable module, as a device driver, and/or in every and any other way known now or in the future in computer programming. Additionally, the present techniques and technologies are in no way limited to implementation in any specific programming language, or for any specific operating system or environment. Accordingly, the disclosure of the present techniques and technologies is intended to be illustrative, but not limiting.

What is claimed is:

1. A method comprising:
   transmitting a low-resolution video stream;
   buffering a high-resolution video stream in a buffer memory;
   receiving a request for the high-resolution video stream, the request including beginning and ending frame numbers based on the low-resolution video stream;
   retrieving the high-resolution video stream from the buffer memory via a synchronizer, wherein the synchronizer synchronizes the low-resolution video stream and the high-resolution video stream to a same relative time; and
   transmitting the high-resolution video stream.

2. The method of claim 1, further comprising:
   receiving a device stream; and
   encoding the device stream into the low-resolution video stream and the high-resolution video stream.

3. The method of claim 1, wherein the low-resolution video stream is a medical imaging scan.

4. The method of claim 1, wherein the beginning and ending frame numbers are determined based on an interest of a viewer in a part of the low-resolution video stream.

5. The method of claim 4, further comprising:
   detecting the interest of the viewer in a part of the low-resolution video stream based on the viewer pausing the low-resolution video stream.

6. The method of claim 4, further comprising:
   detecting the interest of the viewer in the part of the low-resolution video stream based on the viewer slowing the low-resolution video stream.

7. A system comprising:
   one or more processors; and
   a memory storing instructions that, when executed by the one or more processors, cause the system to:
      transmit a low-resolution video stream;
      buffer a high-resolution video stream in a buffer memory;
      receive a request for the high-resolution video stream, the request including beginning and ending frame numbers based on the low-resolution video stream;
      retrieve the high-resolution video stream from the buffer memory via a synchronizer, wherein the synchronizer synchronizes the low-resolution video stream and the high-resolution video stream to a same relative time; and
      transmit the high-resolution video stream.

8. The system of claim 7, the memory storing instructions that, when executed by the one or more processors, further cause the system to:
   receive a device stream; and
   encode the device stream into the low-resolution video stream and the high-resolution video stream.

9. The system of claim 7, wherein the low-resolution video stream is a medical imaging scan.

10. The system of claim 7, the memory storing instructions that, when executed by the one or more processors, further cause the system to halt transmission of the low-resolution video stream.

11. The system of claim 10, the memory storing instructions that, when executed by the one or more processors, further cause the system to resume transmission of the low-resolution video stream.

12. The system of claim 7, wherein the beginning and ending frame numbers are determined based on an interest of a viewer in a part of the low-resolution video stream.

13. The system of claim 12, the memory storing instructions that, when executed by the one or more processors, further cause the system to:
    detect the interest of the viewer in the part of the low-resolution video stream based on the viewer pausing the low-resolution video stream.

14. The system of claim 12, the memory storing instructions that, when executed by the one or more processors, further cause the system to:
    detect the interest of the viewer in the part of the low-resolution video stream based on the viewer slowing the low-resolution video stream.

15. A computer program product comprising a non-transitory computer useable medium having a computer-readable program, wherein the computer-readable program, when executed on a computer, causes the computer to:
    receive a low-resolution video stream;
    transmit a request for a high-resolution video stream, the request including beginning and ending frame numbers based on the low-resolution video stream; and
    receive the high-resolution video stream via a synchronizer, wherein the synchronizer synchronizes the low-resolution video stream and the high-resolution video stream to a same relative time.

16. The computer program product of claim 15, wherein the computer-readable program, when executed on a computer, further causes the computer to transmit a request to halt the low-resolution video stream.

17. The computer program product of claim 16, wherein the computer-readable program, when executed on a computer, further causes the computer to transmit a request to resume the low-resolution video stream.

18. The computer program product of claim 17, wherein the request to resume the low-resolution video stream is generated upon completion of receiving the high-resolution video stream.

19. The computer program product of claim 15, wherein the beginning and ending frame numbers are determined based on an interest of a viewer in a part of the low-resolution video stream.

20. The computer program product of claim 19, wherein the computer-readable program, when executed on a computer, further causes the computer to:
    detect the interest of the viewer in the part of the low-resolution video stream based on the viewer pausing the low-resolution video stream.

* * * * *